(12) United States Patent
Deshpande et al.

(10) Patent No.: US 9,080,989 B2
(45) Date of Patent: Jul. 14, 2015

(54) WHISKER MANUFACTURING, DETECTION, RESPONSE, AND COMPOUND MANUFACTURING APPARATUS AND METHOD

(71) Applicant: The United States of America as represented by the Secretary of the Navy, Washington, DC (US)

(72) Inventors: Nishkamraj U. Deshpande, Novi, MI (US); James E Schwabe, Bedford, IN (US); H Fred Barsun, Bloomington, IN (US); Nancey J Maegerlein, Williams, IN (US); Norris J Caldwell, Bloomington, IN (US); William W Fultz, Carmel, IN (US); Lloyd W Zilch, Bloomington, IN (US); Samuel G Stuart, Bloomington, IN (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 14/327,162

(22) Filed: Jul. 9, 2014

(65) Prior Publication Data

US 2015/0070691 A1    Mar. 12, 2015

Related U.S. Application Data

(60) Provisional application No. 61/844,327, filed on Jul. 9, 2013.

(51) Int. Cl.
| | | |
|---|---|---|
| *G01N 21/00* | (2006.01) | |
| *G01N 21/95* | (2006.01) | |
| *C25D 5/48* | (2006.01) | |
| *C25D 3/30* | (2006.01) | |
| *C23C 8/12* | (2006.01) | |
| *C23C 28/04* | (2006.01) | |

(52) U.S. Cl.
CPC ......... *G01N 21/95* (2013.01); *C23C 8/12* (2013.01); *C23C 28/04* (2013.01); *C25D 3/30* (2013.01); *C25D 5/48* (2013.01); *G01N 2201/088* (2013.01)

(58) Field of Classification Search
USPC ............... 356/237.1–237.6, 239.1–239.8
See application file for complete search history.

(56) References Cited

U.S. PATENT DOCUMENTS

2008/0291451 A1* 11/2008 Cheng et al. ............... 356/433

* cited by examiner

*Primary Examiner* — Tri T Ton
(74) *Attorney, Agent, or Firm* — Christopher A. Monsey (57) ABSTRACT

An invention for making productive uses of normally undesirable whiskers is provided. Embodiments of the invention include a variety of apparatuses and methods associated with forming and using whiskers as well as forming whisker compounds is disclosed. For example, whisker detection modules can be created which provide a whisker surveillance capability. The whisker detection modules can further be coupled with a whisker response system such as an alarm or insulating material dispersing system. Another aspect of the invention is providing a variety of environments or microenvironments with regard to a whisker forming structure to affect whisker creation such as maximizing whisker formation. Another example includes provision of a variety of embodiments for manufacturing compounds of whiskers of various metal and metal alloys, including structures and methods is provided. Whisker compounds produced using various embodiments of the invention can be used for various applications.

8 Claims, 6 Drawing Sheets

WHISKER MANUFACTURING, DETECTION, RESPONSE, AND COMPOUND MANUFACTURING APPARATUS AND METHOD

CROSS-REFERENCE TO RELATED APPLICATIONS

The present application claims priority to U.S. Provisional Patent Application Ser. No. 61/844,327, filed Jul. 9, 2014, entitled "WHISKER MANUFACTURING, DETECTION, RESPONSE, AND COMPOUND MANUFACTURING APPARATUS AND METHOD," the disclosure of which is expressly incorporated by reference herein.

STATEMENT REGARDING FEDERALLY SPONSORED RESEARCH OR DEVELOPMENT

The invention described herein includes contributions by one or more employees of the Department of the Navy made in performance of official duties and may be manufactured, used and licensed by or for the United States Government for any governmental purpose without payment of any royalties thereon. This invention (Navy Case 102,717) is assigned to the United States Government and is available for licensing for commercial purposes. Licensing and technical inquiries may be directed to the Technology Transfer Office, Naval Surface Warfare Center Crane, email: Cran_CTO@navy.mil.

BACKGROUND AND SUMMARY OF THE INVENTION

The invention relates to creating productive uses, e.g., detection systems or compound manufacturing, associated with formation or nucleation and growth of hair-like protrusive metal structures that have been observed to form from a variety of metals and/or alloys. These hair-like or protrusive metal structures are sometimes described as whiskers. Whiskers are normally viewed as undesirable emergent structures associated with use of a variety of compounds in electronic device manufacturing such as tin. The cause of whisker formation has been hypothesized but not clearly proven thus there is a substantial degree of uncertainty associated with whisker formation. A large number of defects are associated with whisker formation. Attempts to eliminate whisker formation have largely failed including creation of manufacturing processes where lead use is avoided. Widespread experimentation and research have failed to provide needed results or countermeasures to risks associated with whisker formation.

Disclosed embodiments of the invention include a variety of apparatuses and methods associated with forming and using whiskers as well as forming whisker compounds. For example, whisker detection modules can be created which provide a whisker surveillance capability. Exemplary whisker detection modules can further be coupled with a whisker response system such as an alarm or whisker response system such as activation of a moveable dispenser applying insulating or whisker negating reactive material on a whisker being formed. Another aspect of the invention includes providing a variety of environments or microenvironments with regard to a whisker forming structure to affect whisker creation such as mirroring an environment associated with a part under whisker surveillance or maximizing whisker formation. Another example includes provision of a variety of embodiments for manufacturing compounds of whiskers of various metal and metal alloys, including structures and methods is provided. Whisker compounds produced using various embodiments of the invention can be used for various applications.

For example, one aspect of the invention includes a method to manufacture different types of compounds of whiskers generated from the electroplated surfaces/substrates of metals and the alloys of the metals, such as Tin (Sn) and many other low melting metals such as Zinc (Zn), Silver (Ag), Gold (Au), Cadmium (Cd), Aluminum (Al), Lead (Pb), Indium (In), in diameters scales ranging from nm to mm and in lengths up to 10 mm or more. Formation and occurrence of these metal whiskers protruding out of soldered areas of microelectronic devices are nuisance to electronic circuits which cause short circuit failures, but their compounds such as $SnO_2$, $ZnO$, etc, in various forms and generated from non-electroplated substrates have been researched and employed in various applications such as gas sensors or anodes for lithium ion batteries, etc. These nano (nm)/micro (μm) sized needle shaped compounds are made by various non-electroplating techniques. These various techniques do not use the needle shaped whiskers generated from electroplating process to intentionally produce chemical compounds such as oxides, nitrides, carbides, sulphides, hydrides, or any complex compounds thereof such as carbonitrides, or sulphates etc. by generating the metal or metal alloy whisker and subsequently reacting them in various environment such as Carbon, (C), Nitrogen (N), Sulfur (S), Oxygen (O), Hydrogen (H) or their combinations to generate whisker compounds. Considering above the present innovation specifically focuses at intentionally creating whiskers of various metals such as Tin (Sn), Zinc (Zn), Silver (Ag), Gold (Au), Cadmium (Cd), Aluminum (Al), Lead (Pb), Indium (In) and alloys of the metals, and chemically reacting the generated whiskers in various gaseous or liquidous environments with various elements such as O, C, S, N, H or their combinations, with the objective to form their whisker compounds such as $SnO_2$, $ZnO$ etc. or generating any organometallic compounds of the whiskers. The above said whisker compounds can be used for any suitable application such as gas sensors for $SnO_2$ or anodes for lithium ion batteries such as $SnO_2$, or $ZnO$ whiskers as battery components. Thus any application that uses the whisker compounds produced by the above mentioned manufacturing procedure involving generation of whiskers from an electroplating process and subsequent/simultaneous chemical reaction of the whiskers with an exposed environment will be encompassed by aspects of exemplary embodiments of this innovation. The exemplary process stated above in this innovation does not bound the whisker compound by extent of the chemical reaction of the electroplating produced whisker with the exposed environment, or size and shape of the original pure metal or metal alloy whisker, and the whisker compound generated.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The foregoing aspects and many of the attendant advantages of this invention will become more readily appreciated as the same become better understood by reference to the following detailed description when taken in conjunction with the accompanying drawings.

DETAILED DESCRIPTION OF THE DRAWINGS

The embodiments of the invention described herein are not intended to be exhaustive or to limit the invention to precise forms disclosed. Rather, the embodiments selected for description have been chosen to enable one skilled in the art to practice various embodiments of the invention.

Figure 1:
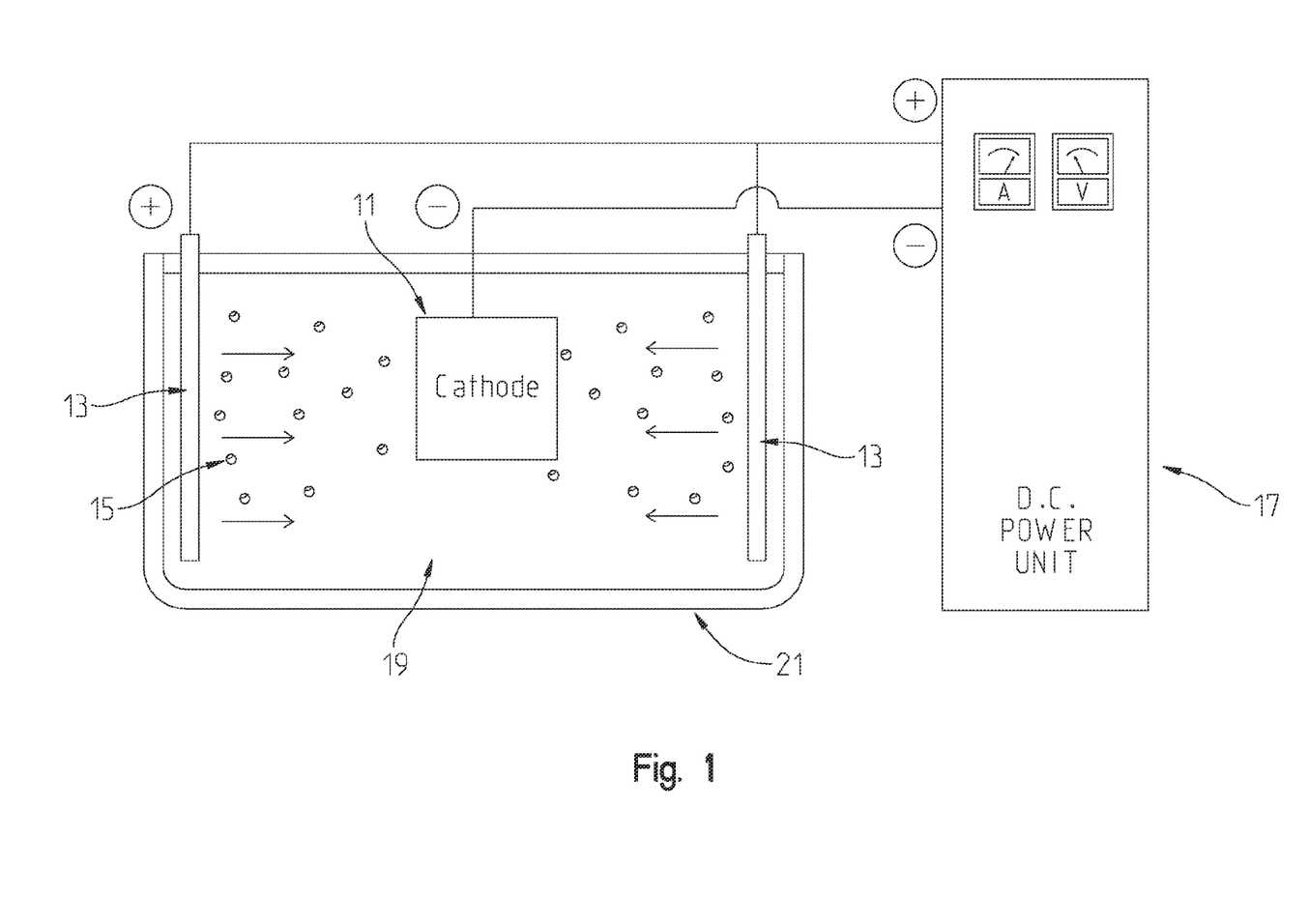
FIG. 1 shows a diagram of a electroplating bath as a whisker generating system according to one exemplary aspect of an illustrative embodiment of the invention.

Referring initially to FIG. 1, whiskers of various metals such as Tin (Sn), Zinc (Zn), Silver (Ag), Gold (Au), Cadmium (Cd), Aluminum (Al), Lead (Pb), Indium (In) and/or alloys of metals can be plated on a substrate 11 by employing metals/or alloys as an anode 13 and thus electroplating or electrochemically forming the anode material in whisker form on a suitable cathode substrate 11. Employment of metals or alloys can be done by using a suitable electrolyte 19 and power supply 17 to produce ions 15 of the anode material 13 for application on the cathode 11. Metals or alloys used to form whiskers can also be selected or formed to have or generate mismatches of coefficient of thermal expansion between a plating material and substrate. Plating thickness can also be controlled to maximize whisker growth for a particular combination of plating chemistry, substrate material(s), grain structure and environmental conditions. Compounds, such as brighteners, which tend to increase or alter whisker formation, can be selected for inclusion into a plating material. Specific substrates can be selected to have an increased effect on whisker growth such as brass as a substrate for tin. A substrate can also have structures built in which influence whisker formation such as temperature altering structures, e.g., heating or cooling structures, as well as mechanical stress induction sections e.g., piezoelectric structures, which influence whisker formation.

Figure 2:
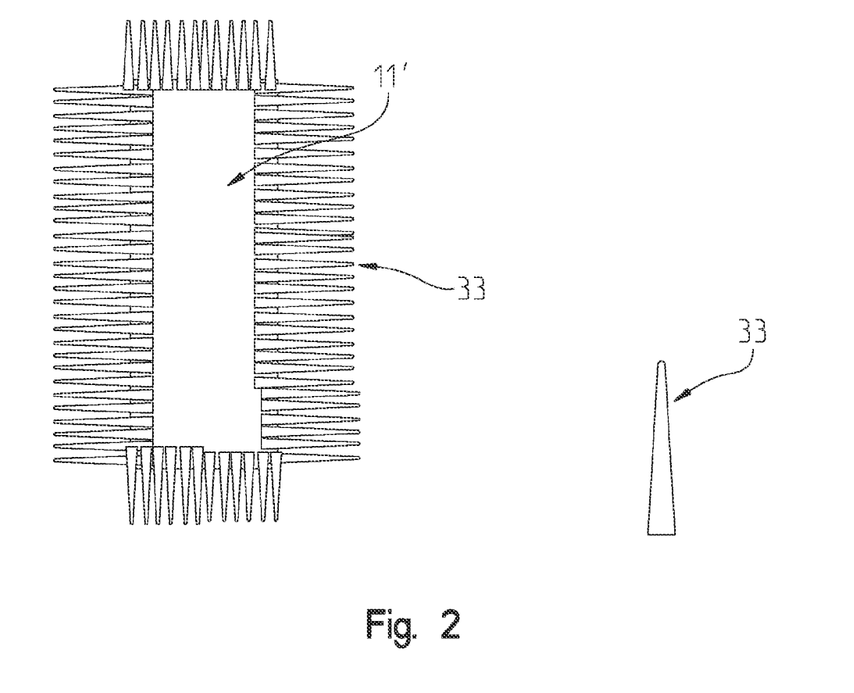
FIG. 2 shows a diagram of an exemplary whisker material formed on the exemplary cathode substrate shown in FIG. 1 according to an illustrative embodiment of the invention.

Referring to FIG. 2, after electroplating the anode material/s 13 on substrate 11, the electroplated substrate/coating assembly can be removed from an electrochemical structure, such as, for example, the electrolytic bath 21. The substrate/coating assembly would then be exposed to suitable environments to allow the nucleation, growth and protrusion of whiskers, e.g., needle like whiskers. Factors such as an increase in boundary grain diffusion of a material which is intended to promote growth of whiskers thereon or in relation to as well as altering or adjusting environmental temperature and humidity can enhance the occurrence of whiskers. Accordingly, microenvironments or localized whisker formation substrate or formation structures can be created at specific locations on substrate 11' which increases or adjusts whisker formation on the substrate. Such microenvironments may be created by means of application of one or more coatings on the substrate or by means of application or positioning of a microenvironment structure on the substrate 11' which is then injected or controlled with a particular environmental condition such as temperature, humidity, or other aspect that can influence a microenvironment within the microenvironment structure (not shown). For example, a microenvironment structure can be formed with different chambers that have an open wall where the structure section with the open wall can be placed in contact with substrate 11' then a desired environment can then be created within the different chambers by means of either inlet ports or actual environmental generators which are in communication with the chambers. Different microenvironments can be created with different gasses such as hydrogen sulfide being applied in the presence of silver. For example, an environmental generator might be a heating element or a source of generating humidity such as a sonic generator which vaporizes water upon injection into a chamber. Different conditions then can be measured and controlled in the different chambers or microenvironments. Other possibilities for forming microenvironments include probes or control structures which generate conditions in proximity to a specific point of a substrate such as an air flow with desired humidity or lack thereof which creates laminate airflows of the substrate along with a different probe which injects a desired atmosphere between the airflows that separate micro environmental conditions. An exemplary embodiment of the invention can also induce cyclical material stress inducers or temperature cycling to generate whisker growth. Another probe structure can be a heating structure (note shown) used to generate specific heat spots or heating of specific areas of anode material formed on a substrate which then influence whisker growth. Another aspect of the invention can include a system which has an array of whisker affecting materials which can be injected into a particular environment or microenvironment which can be selectively applied to adjust or control whisker formation. For example, different pressures or densities of whisker inducing compounds can be injected via injection ports or moveable application systems. Mixing systems or chambers can be used as well to combine materials before injection.

Another whisker formation structure (not shown) or microenvironmental control structure (not shown) can be one that induces physical stress, compressive stress, bending/stretching of part or all of the substrate, or maximizes residual stress into a substrate and anode material before, during, and/or after formation of anode material on a substrate. Another whisker formation structure or micro environmental control structure (not shown) can include a structure to control or manipulate whiskers as they form to control their position or movement so as to bend the whisker structures due to forces such as electrostatic attraction. This structure to control or manipulate whiskers can be used to manipulate formation of such whiskers to increase or control whisker formation. In general, whiskers, sometimes referred to as protrusions or structures including hair-like structures, can be formed to include nodules, filaments, solid/striated, circumferential rings, or a structure with kinks/bends.

In this application, the anode 13 material is distributed into the electrolyte using the apparatus shown in FIG. 1 however a specific formation or application of anode material 13 can also be provided for to produce a desired formation of whiskers in specific locations, densities, and forms. Another structure can be provided which retards or eliminates formation of whiskers in specific locations while increasing them in others in order to obtain a specific or predetermined shape or quantity of whiskers in particular locations, dimensions, or forms.

Figure 3:
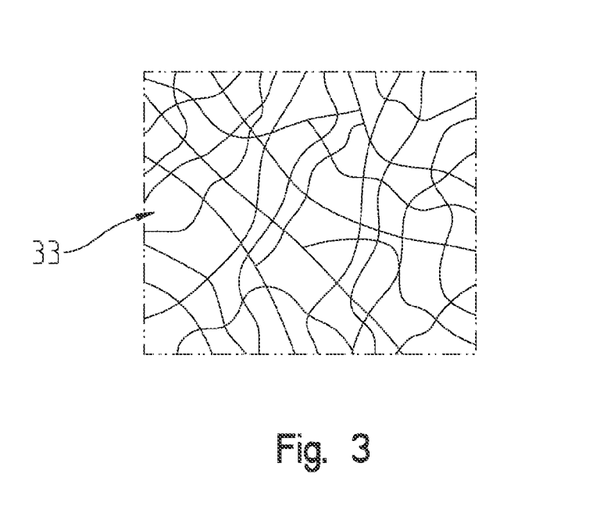
FIG. 3 shows a diagram of an exemplary whisker material formed on the cathode substrate shown in FIG. 1 according to an illustrative embodiment of the invention.

Referring to FIG. 3, a process and structure is used to obtain a whisker product on a substrate 11'. FIG. 3 also includes a detail view, shown as whisker formation needles 33 which are formed on substrate 11/11'. The FIG. 3 description is shown as a simplified structure, e.g., 11', in accordance with one aspect or embodiment having a coating of anode material 13. FIG. 3 shows needles of whiskers as produced using, for example, electroplating process that may or may not be coupled with a whisker inducing activity, e.g., environmental exposure.

Another exemplary embodiment of the invention could include an application having a whisker detection module (WDM) (not shown) which emulates environmental conditions for a device under whisker surveillance (DUWS). A WDM can be formed as a hardware-in-the-loop simulator which can create various approximations of DUWS as well as a fully blow system which has part or all of a DUWS in a controlled environment. Multiple WDMs can be used for the same DUWS with matching DUWS environment in order to increase detection accuracy. A prediction system can also be created which can alter conditions associated with an actual DUWS within a testing or reaction chamber which then can be used to predict whisker formation in different scenarios including application of different testing factors such as electrical power, mechanical stress, humidity, application of electric fields, impacts, temperature variations as well as cycling of one or more of these testing factors.

Remote sensors can be networked with the test system which then receives real time information from one or more DUWS in actual storage or field use. This system can be used with, for example, a sampling of vehicles, aircraft, satellites, etc which are in actual use and have telemetry systems which send DUWS condition updates to the testing system e.g., WDM. For example, an on-board system in a vehicle could have sensors positioned in relevant areas such as, e.g., accelerator pedals, which then could be transmitted to a telemetry system. An embodiment of the invention can also have a system which alerts maintenance personnel as well as operators by means of a messaging system which sends status updates as well as warning signals which can be triggered by a combination of environmental factors as well as detection of patterns of DUWS behavior which have been associated with whisker formation as a precursor to a device failure. Thus, whisker detection can be positioned not only with the WDM but also with the DUWS. An embodiment of the invention can then be used to correlate testing or monitoring results from both WDM and the DUWS and display/store such data for diagnostics and response actions which can be either user generated or a trigger for a whisker response system.

An embodiment of the invention can also be directed towards DUWS within a containment shell that is both highly sensitive and highly reliable and does not create conditions during operation which might influence whisker formation. It is also desirable to ensure that sensor systems themselves are not vulnerable to whisker formation. Such sensors would need to be designed so they are not themselves subject to breakdown or false readings from whisker formation. Moreover, it is important to ensure that sensor system operation does not create an unpredictable influence on a DUWS or WDM system. Another exemplary system can include an ability to measure and transfer environmental data to the system outside a containment structure which would not interfere with highly sensitive and reactive devices within a portable but isolated containment shell, for example by introducing radio frequency (RF) interference into the system under test. An exemplary system can be designed to avoid creating electromagnetic (EM) interference, have an electromagnetic presence, or generate an EM field/signature. An exemplary system may also be designed to be immune from EM fields that are created in the vicinity of the test system. Also, it may be designed to address deficiencies in existing systems such as a problem with piezoelectric sensors (e.g., require periodic recalibration). Since these containers are sealed, a desired monitoring needed to show exactly what conditions have occurred within the container. For example, conditions monitored conditions could include temperature, humidity, vibration, and shock. An exemplary container would have individual monitoring given containers can be in groups of multiple containers and can sometimes be swapped out individually. Moreover, individual container monitoring addressed a variety of factors such as how one container on one side of a group might be too hot, while another is too cold, etc.

Another consideration was a requirement that highly precise devices stored in sealed containers for lengthy time periods were required to function properly after being stored in the containers without periodic maintenance for multiple years. These devices had precision systems that were calibrated when they were sealed in the container, but the calibration could be thrown off due to a variety of factors such as high temperature or sudden shock. An exemplary system could further be designed so that each container could be monitored continuously and store sensor readings. Another useful aspect of an embodiment of the invention is that data could be shown to a vendor of the device for warranty purposes. Stored data could also be used for maintenance decisions such as determining when systems stored within exemplary containers did not meet various system or reliability thresholds or standards. Measurement of humidity and data temperature taken outside of a container was not helpful given there was no guarantee that conditions inside of a container matched external conditions. For example, maintenance systems which calculated a number of days where the ambient temperature exceeded a threshold temperature that was used to infer degradation of a system stored within a container resulted in replacement of a system which did not actually need replacement and vice-versa.

In one embodiment a payload could be sensitive to electromagnetic and/or RF emissions. For example, a payload of a container can be sensitive to electromagnetic and/or RF emissions and thus the sensors need to be purely optical-based. In one embodiment, the tolerance data is provided by a manufacturer of a payload. In another inventive variant, readings of sensors can be forwarded to maintenance organizations responsible for payloads in the containers to assist in making decisions on replacement of payloads. In an additional inventive variant, an exemplary computer program runs on a computer whose temperature is being monitored by a logging device and reporting to a computer program.

One embodiment of the invention can include an equipment and asset monitoring system whose operational objective is to continuously and autonomously monitor, record, and assess environmental conditions and equipment status; transfer the information to a remote location; and use the information for immediate or future design, maintenance, or reliability decisions. An embodiment can include a central processor, data acquisition units, and sensors. Exemplary sensors can be optical and/or powered. Optical sensors in accordance with one embodiment of the invention can be small, lightweight, accurate, reliable, unpowered, noncorrosive, and intrinsically safe which can be used for monitoring within sealed containers containing sensitive payloads. Sections of the sensors which may be vulnerable to whisker formation can be specifically designed to eliminate or mitigate whisker formation e.g., by using lead rather than tin in component design. Another benefit of optical sensors in accordance with one embodiment is that once they are calibrated, no recalibration is required.

Another embodiment can include all-optical, all-powered, or a combination ("hybrid") of sensors. A system can be compatible with Local Access Networks (LANs) to support data transfer to or from remote locations. One embodiment can monitor four environments: Temperature; Relative Humidity; Vibration; and Shock.

Monitored data can be used to more accurately define the actual field environment, to ensure design parameters are valid, and to better estimate equipment and asset reliability. An embodiment of the invention provides actual, empirical data where it actually is and this system accumulates it for the entire time it is in service. Data collected can aid root failure analysis e.g., the part was too hot, thus the location it was placed into became too hot and a new location or more cooling is needed in the future.

An embodiment of the invention can include software created/adapted using LabView software. An exemplary graphical user interface (GUI) can be created to give a birds-eye view of a module area; each exemplary module has eight canisters—an exemplary canister has a door on them. An operator of an exemplary system can monitor eight groups of eight different square boxes; each exemplary box has a device in it. An exemplary system can use red, yellow, green light to reference a container with instruments which indicate an environment or micro-environment within a container is within parameters. For example, if all exemplary parameters inside of an exemplary container are in tolerance—e.g., temp, humidity, shock, vibration then a sensor status light will show green. Where a system environment is out of tolerance, an exemplary system turns a status light red. An exemplary system gives go/no go for monitored containers to give a user or operator of a system which uses stored payloads an indication of reliability of stored payloads and whether or not such a system should or should be used or deployed. If an operator desires more information, an operator can select the red light using a GUI/mouse or equivalent to show an entire container with sensors at different spots. In this example, each spot has a digital display i.e. location, temp, humidity, shock, vibration. IF a parameter is out of limits, an exemplary system will indicate a relevant current readout associated with the red signal. An operator can use a GUI to select any sensor location for more information. An operator can also produce a digital readout and a history for that sensor—e.g., 24 hours, 48 hours etc. An operator can also obtain a graph of when a monitored system was out of tolerance.

For the users or maintenance personnel in remote locations away from monitored payloads, an exemplary system can be configured to transmit all or a subset of monitored information and history. An exemplary system can include a software program which generates an out-of-tolerance file which is transmitted or saved to the people at such remote locations. Transmission can be done via a communication network which, for example, provides auto alerts to a depot/maintenance personnel which apprises them of a need to take action on an out-of-tolerance event. Remote personnel can communicate with a payload user or operator and advise them to take an action e.g., verify heating or cooling systems working properly. An embodiment of the invention can reduce costs, provide information to make maintenance action decisions, increase reliability, and improve asset or payload availability.

An embodiment of the invention can also be used to address impact damage which might influence whisker formation or have secondary benefits. For example, if monitored containers were in an area that suffered an earthquake or an accident during shipping, an embodiment of the invention would alert maintenance and user personnel of an out-of-parameter or threshold event, e.g., damage to payload or containers. An embodiment of the invention could also immediately alert user or maintenance personnel to which devices were not capable of functioning as designed. An embodiment of the invention can inform users or maintenance staff which unit or payload must be removed for maintenance after an out of tolerance/threshold/parameter event e.g., impact or major vibration damage, occurs. The invention permits users or maintenance staff to determine what payloads can and cannot be used with a high reliability.

Sensors can include fiber optic sensors with a required dynamic range e.g. accelerometer that uses fiber optics. An exemplary instrumented canister can be connected to exemplary optical sensing interrogators for, e.g., vibration-shock and temperature-humidity via fiberoptic cable. Fiberoptic cable may be preferred because it can be used over long distances without loss of signal. Exemplary optical sensing interrogators can communicate with an exemplary monitoring computer via an Ethernet connection. An exemplary equipment monitor can comprise a data logger, such as a Pace XR5 Data Logger, which acquires exemplary temperature of the exemplary monitoring computer and reports it back to the exemplary monitoring computer. Exemplary optical sensing interrogators operate by means of use of a swept laser which sends its signal at programmed time intervals through a coupler. The exemplary coupler sends an exemplary signal to, for example, both a 1×4 multiplexer and a picowave controller. Exemplary 1×4 multiplexer transmits exemplary signal to exemplary detector modules. Exemplary picowave controller can send exemplary signal(s) to an exemplary signal processor. The exemplary signal from exemplary detector module and exemplary picowave can be compared and exemplary results are sent by the exemplary detector module out to the exemplary sensors. Optical sensor for, e.g., temperature and relative humidity, in a sealed container can include provision of an exemplary optical fiber strung throughout the exemplary sealed container or area of interest with a DUWS. Readings can be taken at a variety of locations. These readings can be used to calculate what exemplary temperature and relative humidity in exemplary sealed container are.

An exemplary layout of exemplary accelerometers to detect, e.g., vibration and shock in a sealed container can include provision of an optical fiber is laid out throughout an exemplary sealed container. A variety of fiber optic accelerometers can be attached to a DUWS or a WDS or a containment structure, e.g., a closed structure or another structure such as a vehicle, for a DUWS/WDS. For example, several accelerometers can be placed at one end of an exemplary container or containment structure and three at exemplary other locations. Sensor lines can be strung along an exemplary container, containment structure, or sealed container. For example, one Tri-Axial IEPE Accelerometer can be attached to each end of an exemplary sensor line. A user interface can include a display of exemplary information available in real time for an individual container. A display can also show how a reading, e.g., humidity condition, is outside of tolerance as shown, e.g., by a colored outline (red for example). Actual numbers of readings can be shown to give an operator an idea of how far in or out of tolerance different readings are. An embodiment of the invention thus can provide a wealth of systems which work under the circumstances discussed above and below.

An exemplary WDM can include a whisker test structure (WTS) that is manufactured with the same or similar materials (as well as all or some of the same manufacturing processes) as the DUWS. The WTS could also be made from portions of an actual DUWS. The WDM can include environmental controls and/or micro-environment creating sections which interact with the WTS so that the WTS has a same or similar condition and environment as the DUWS. The WDM receives inputs from sensors associated with the WTS and responds accordingly. A sensor system can be implemented with the WDM that is adapted to detect different aspects of a whisker which is growing on the WTS such as a light sensor and a moveable light which is rotated at different angles with regard to surfaces of the WTS that detects a different refraction response for specific regions of the WTS than a pre-whisker growth condition on the WTS. A look-up table is provided which is used to compare actual readings to a pre-whisker growth reading. Another possible whisker sensor can be application of high voltage to the WTS which then generates a plasma discharge when the whisker short circuits with a plurality of grounding structures surrounding the WTS. Such a short circuit would then generate an alarm which could then be used to trigger a response with regard to the DUWS. Whisker responses can include application of an insulating compound to all or parts of the DUWS, remote application of an ultrasonic probe/vacuum to a corresponding area of the DUWS associated with the WTS (where the structures are the same or similar), application of range switching to deliver whisker-melting impulses to circuits of interest in proximity to a targeted whisker (e.g., corresponding to the portion of the DUWS correlated to a whisker on a WTS), a power down of sensitive components or circuits that are in proximity to a whisker on the DUWS or predicted area of interest on the DUWS related to the detected whisker on a WTS, summoning maintenance personnel/robotic repair equipment, etc. A WDM can include multiple compartments having a same or similar component in order to obtain a multiple verification system activated when more than one same or similar WTS has a detected whisker. A WDM embodiment can also have separate whisker inducing control systems which provide sensing or monitoring of whisker condition equivalent areas of a single or multiple DUWS items.

Figure 4:
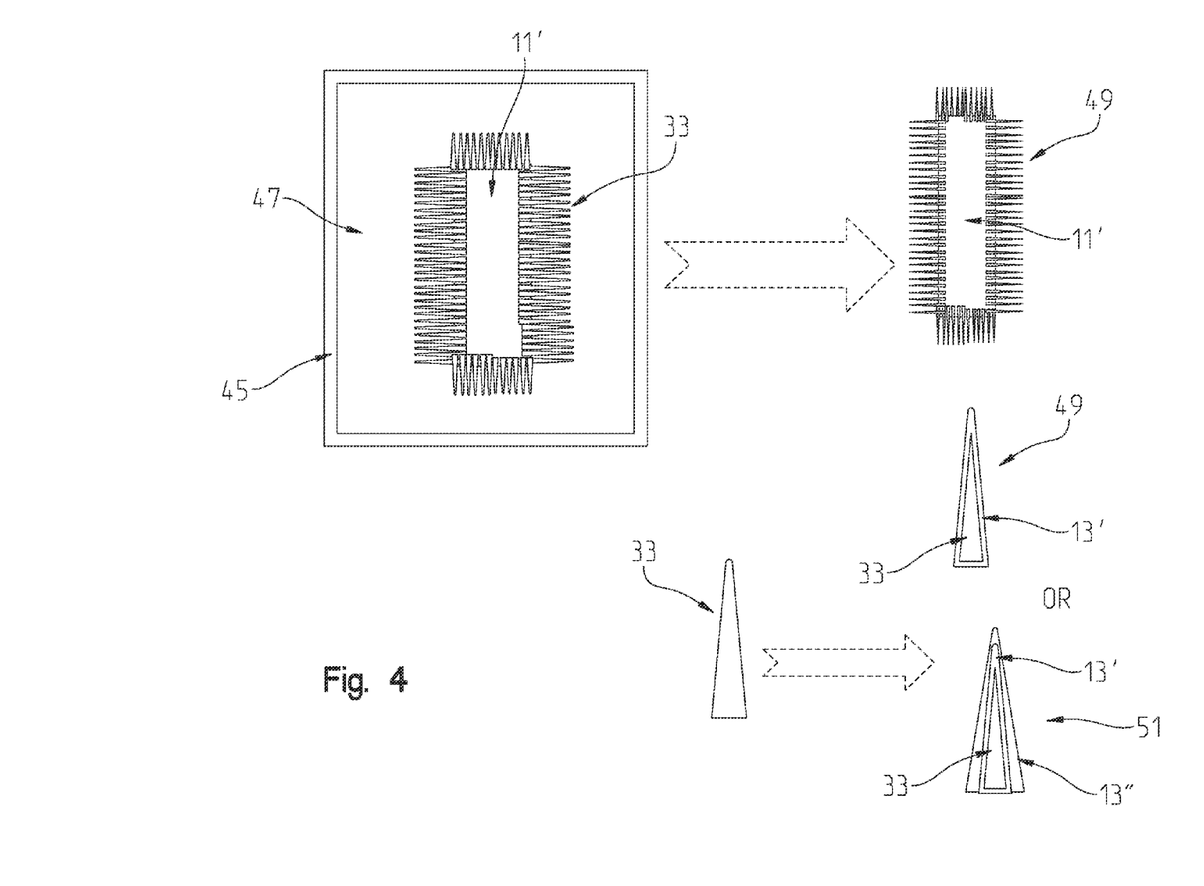
FIG. 4 shows an overview diagram of an exemplary whisker compound (e.g. oxide) manufacturing progression according to an illustrative embodiment of the invention as well as a detailed or enlarged view of a whisker compound formation structure shown in the overview diagram which illustrates formation of a whisker compound formation layer according to an illustrative embodiment of the invention.
Figure 5:
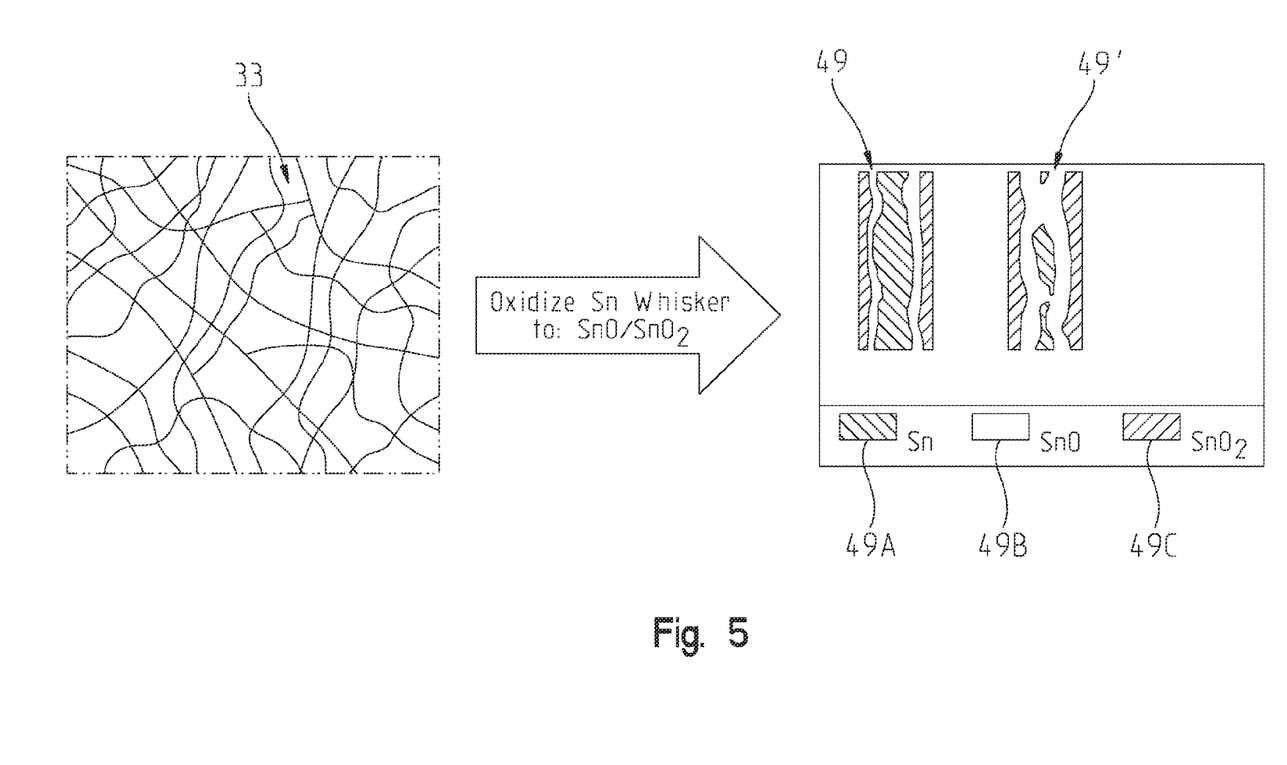
FIG. 5 shows a diagram of a of whisker compound or structure as manufactured according to an illustrative embodiment of the invention.

Referring to FIGS. 4 and 5, a generalized graphical depiction of a step-wise process is shown. FIGS. 4 and 5 show an exemplary placement of whisker forming needles substrate assembly (11' and 33) into a reaction chamber 45 containing suitable environment 47 (such as carbon and/or oxygen and/or sulfur or any other suitable environment), to react with forming whisker needles 33 to create whisker needles 33 having a coating or composition 13'/13" which formed a new whisker compound 49 on the whisker forming needle(s) 33. FIG. 4 also shows another multi-laminate, composite, or intermixed type of whisker structure 51 embodiment (substituted for 49 relative to substrate 11') comprising a plurality of whisker forming needles 33 having multiple or mixed layers (13'/13"). The FIG. 4 multi-laminate, composite, or intermixed type of whisker structure 51 can be formed by application of multiple processing steps as well as by use of more than one reactant compound or a variety of reactant compounds. A single, mixed, or multilayered whisker compounds formed with or using single or more than one material can be created by a series of processing steps.

FIG. 5 shows oxidation of a tin (Sn) 49A whisker to a tin oxide (SnO) 49B and then tin dioxide ($SnO_2$) 49C. For example, processing steps in accordance with one embodiment of the invention can include interacting a whisker product based on suitable reaction parameters, e.g., in a reactive atmosphere having a reactant compound such as oxygen (O), to generate desired whisker compounds e.g., whisker oxides SnO 49B then oxides as $SnO_2$ 49C as shown in FIG. 5.

Suitable reaction parameters such as temperature, partial pressure, etc can be selected for inclusion into, e.g., reaction chamber 45, in order to create various types of resultant whisker compounds. For example to obtain oxide SnO or $SnO_2$ on a layer (e.g., 49, 51) as shown in FIG. 5, a structure or operator would heat tin nanowires/substrate assembly (11 and 33) in a reaction chamber (45) having air atmosphere (47) at ≈200° C. for approximate 2 hours.

An automation system (not shown), such as a whisker detection module WDM, as well as a WDM which further monitors and controls whisker compound creation or alternation, can also be used to remotely monitor and adjust conditions in an embodiment of the invention. A controller (not shown) can be provided, including one with software, which controls variants of a WDM, such as described herein, to create desires effects including monitoring and controlling reaction parameters associated with use of an exemplary WDM, WTS, and reaction chamber 45. Such a system can also include a user interface (not shown) which provides an operator detection, monitoring, and control capabilities over various aspects of embodiments of the invention such as, for example, the WDM, WTS, and reaction chamber 45. A sensor system can also be provided which provides data on environment(s), surfaces of structures, or materials within and associated with an exemplary reaction chamber (e.g., 45) which can be displayed on a user interface.

A whisker detection alarm as well as a response system can also be coupled to an exemplary embodiment of the invention (not shown). For example, a dispensing or whisker response system can be applied to a detected whisker in or on a DUWS upon detection of a similar whisker on a WTS. A confirmation sensor system can be included or positioned with respect to the DUWS to provide a confirmatory sensor system to verify an actual whisker was actually formed on a DUWS. This confirmatory system might detect an actual whisker that has been formed on a different part of the DUWS by means of a sensor system which can measure or collect surface condition data on different parts of the DUWS. For example, an articulated optical sensor can be moved along with a high power electromagnetic spectrum source which does not cause disruptions to a DUWS (e.g., light) or even an electron microscope which is operated in a safety mode of the DUWS which has been configured to prevent damage when the electron microscope is articulated over its surface. For example, the light source and optical sensor could be configured to rotate and be positioned in a manner adapted to alter a perspective on an area of interest which addresses the substantial difficulty in detecting a whisker such as different profiles and very thin dimensions of whiskers. For example, a sensor system could apply a light source on an axis and then compare an image capture of the DUWS in a known good condition then compare the image capture. The system could then rotate ninety degrees, capture another image during application of the high intensity light source, and perform the same comparison of the second image capture with a corresponding known-good image capture of the same DUWS that was taken using the same sensor along the same axis of view.

Figure 6:
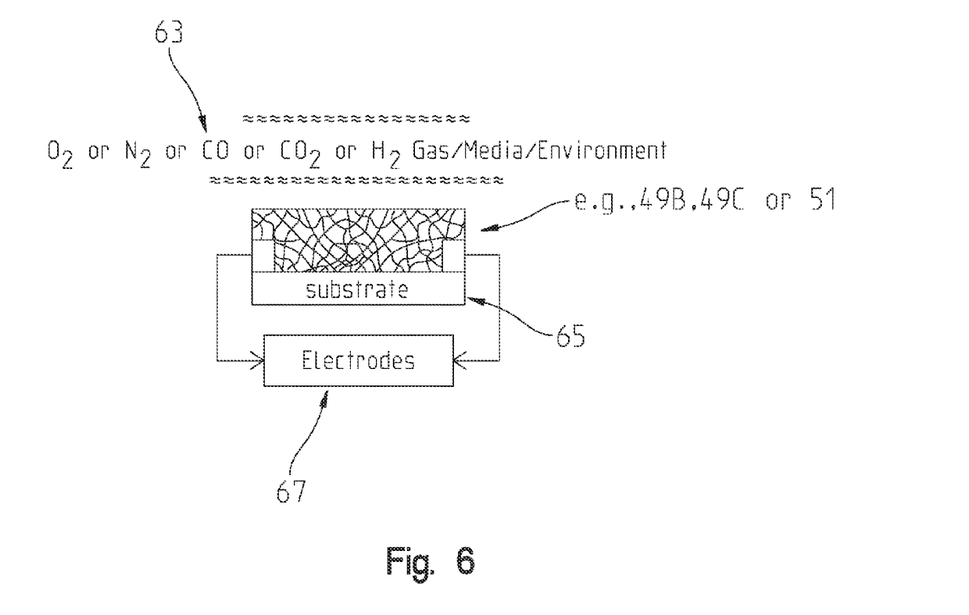
FIG. 6 shows a diagram of an exemplary use of a whisker compound for an application according to an illustrative embodiment of the invention.

Referring to FIG. 6, whisker compounds created for a suitable application such as gas sensors. Once a whisker is grown then interacted with a particular process, such as gas that chemically interacts with a whisker material, the resulting compound can be harvested and used in a desired application. For example, a whisker compound (e.g., 13'/13"/49B/ 49C/51) can be collected by means of an embodiment of this invention and deposited on a gas sensor substrate 67. Gas sensor electrodes 65 are coupled to the whisker compound which electrically interacts (e.g., charge transport) with sensed gas in an environment. The gas sensor is then adapted to detect e.g., an $O_2$ or $N_2$ or CO or $CO_2$ or $H_2$ Gas/Media/ Environment by detecting a change in voltage applied to the whisker compound by means of electrodes 65 and a voltmeter (not shown).

A variety of harvesting structures or techniques (not shown) can be used in accordance with various embodiments of the invention. For example, once whisker compounds are created, ultrasonic systems could be used to shatter or separate the whisker compounds growing on a substrate. Ultrasonic systems can be applied at a resonance frequency of a desired whisker compound so that non-conforming segments which do not meet approximate specifications do not shatter or are less likely to shatter. The shattered or broken-off whisker materials can then be collected via a variety of collection structures (not shown) such as structures which generate airflows to direct such materials to specific collection points e.g., filter/separation system (such as a centrifuge), electrostatic attraction, washes, and/or gravity collection into a collection structure and then used in a follow-on manufacturing process.

Figure 7:
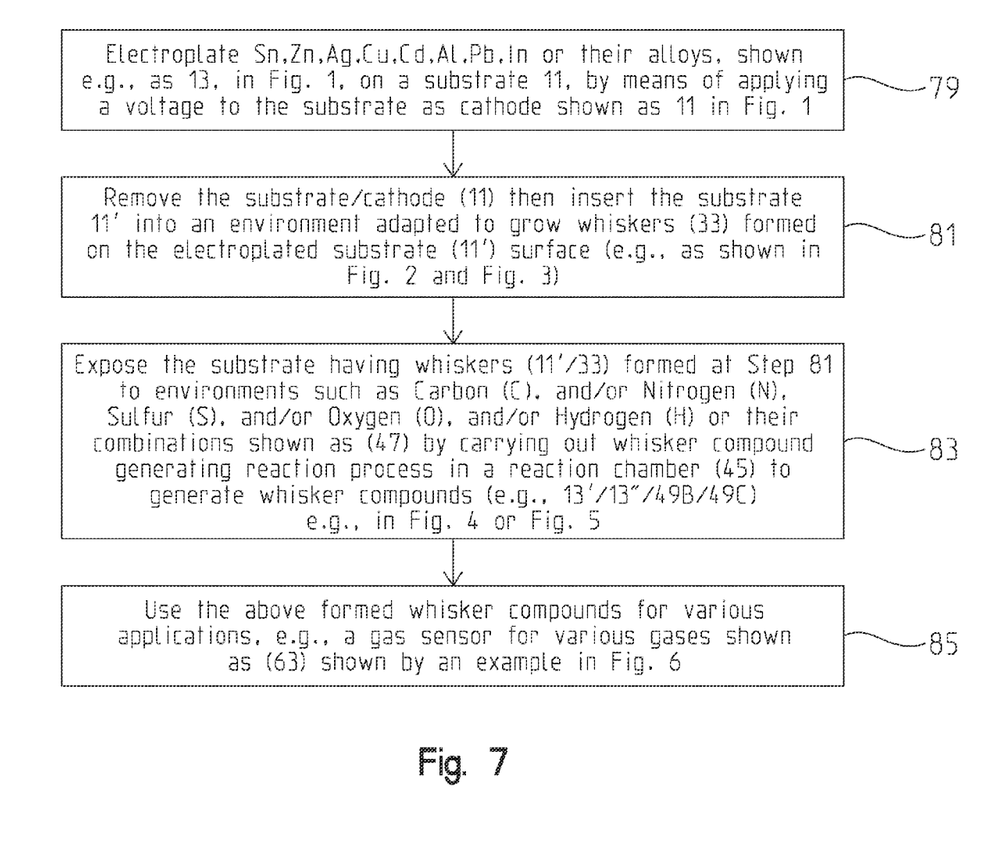
FIG. 7 shows an exemplary diagram showing a whisker compound manufacturing process flow chart in accordance with one illustrative embodiment of the invention.

Referring to FIG. 7, an exemplary method for producing whisker compounds is shown. The process discussed, e.g., in FIG. 4 or 5, can be used. For example, at Step 79, forming a structure which is adapted to nucleate and grow desired whiskers. At Step 81, remove the electroplated substrate/cathode (11') then inserting the substrate 11' into an environment adapted to grow whiskers on electroplated substrate (11') surface as shown, e.g., in FIG. 2 and FIG. 3. At Step 83, once the structure with desired whiskers, e.g., modified 11', has nucleated and grown whiskers, then remove the substrate 11' with whiskers and expose the whiskers to a material or substance to chemically react with the whiskers, e.g., expose to gas to selectively oxidize the whiskers. In particular, at Step 83, expose the substrate having whiskers (11"/33) formed at Step 81 to environments such as Carbon, (C), and/or Nitrogen (N), Sulfur (S), and/or Oxygen (O), and/or Hydrogen (H) or their combinations (47) by carrying out whisker compound generating reaction process in a reaction chamber (45) to generate whisker compounds (e.g., 13'/13"/49B/49C/51) e.g., in FIG. 5 or FIG. 6. For example, an exemplary process to chemically change structures of interest (e.g., whiskers) can be done with an aim of altering electrical, mechanical, or structural characteristics of the whiskers in areas of interest on the substrate 11'. At Step 85, use the above referenced whisker compounds (e.g., e.g., 13'/13"/49B/49C/51) for various applications, e.g., a sensing medium of a gas sensor (for various gases shown as (63) shown by an example in FIG. 6.

In one case, whiskers can be formed, the structure with the electro-formed structures is removed from an electrolyte bath, the electro-formed structures exposed to a material which reacts with the electro-formed structures, e.g., oxidized, and then the structure is placed into a target application such as a battery (e.g., as an anode). In this example, the whiskers alter texture as well as electrical performance of the battery anode in a desirable way such as increasing surface transfer area, improving charge attributes, as well as improving conductivity with the battery to increase battery efficiency.

Although the invention has been described in detail with reference to certain preferred embodiments, variations and modifications exist within the spirit and scope of the invention as described and defined in the following claims.

What is claimed is:

1. A method of manufacturing compounds of various types of metal and metal alloy whiskers comprising:

identifying an application for a material compound which may be formed based on a combination of materials which comprise a first composition of matter, a second composition of matter, and a third composition of matter, wherein said first composition of matter comprises a first material having a first predetermined tendency for nucleation and growth of a protrusive metal structure that erupts outward from a grain or several grains on a metal surface under predetermined formation conditions, said second composition of matter is said protrusive metal structure formed from said first material, said third composition of matter comprises materials that are selected or adapted to chemically react with said second composition of matter to form said material compound upon application of a plurality of chemical reaction steps;

providing a substrate comprising said first composition of matter or a fourth composition of matter that is adapted to receive said first composition of matter that is selected or adapted to have a second predetermined tendency to influence or alter said first predetermined tendency for formation of said protrusive metal structure from said second composition of matter, wherein said substrate is adapted to increase formation of said protrusive metal structure including by means of forming a plurality of protrusions adapted to receive said third composition of matter;

forming said first composition of matter as a coating on said substrate;

forming said protrusive metal structure based on in part adjusting an environment in relation to said substrate formed with said coating to maximize said first or second predetermined tendency said protrusive metal structure will form on said substrate and coating as well as maximizing speed and density of said protrusive metal structure formation;

executing at least a portion of said chemical reaction steps comprising exposing said protrusive metal structures formed on said substrate and coating to said third composition of matter that is adapted to chemically react with said protrusive metal structures to form a plurality of altered said protrusive metal structures comprising said material compound;

separating at least a portion of said plurality of altered protrusive metal structures comprising said material compound from said substrate and coating so as to prevent or minimize damage to said substrate; and collecting said separated at least a portion of said altered protrusive metal structures.

2. A method as in claim 1, wherein said substrate is adapted to have at least part of a form and composition of a device under surveillance.

3. A method as in claim 1, wherein said substrate is formed to induce mechanical stress on said coating to maximize formation of said protrusive metal structures.

4. A method as in claim 1, wherein said substrate is formed with at least one structure adapted to induce a plurality of physical deformations to said coating.

5. A method as in claim 4, wherein said at least one structure is formed with piezoelectric materials and coupled to a controller adapted to induce said plurality of physical deformations based on at least in part said predetermined conditions.

6. A method as in claim 5, wherein said controller is further adapted to induce said plurality of physical deformations based on observing said step of forming said protrusive metal structures and altering said physical deformations to increase formation and density of said protrusive metal structures.

7. A method as in claim 1, further comprising providing a controller and a plurality of non-transitory processing sequences adapted to control said controller and a reaction system said substrate and coating is placed within to form said protrusive metal structures and said material compound, wherein said processing sequences are adapted to monitor said environment and adjust said environment to maximize formation and density of said protrusive metal structures based on outputs of sensors adapted to sense or collect data associated with at least some of said plurality of predetermined conditions.

8. An apparatus for generating whiskers compounds comprising:

- a first structure adapted for forming a material or coating on a substrate, wherein selection of said material or coating as well as said substrate is selected based on a tendency to form whiskers;
- a second structure adapted for adjusting an environment in relation to said whiskers to maximize a probability that said whiskers will form as well as maximizing speed and density of said whisker formation;
- a third structure adapted for exposing said whiskers on said substrate to a material adapted to chemically react with said whiskers to form a plurality of whisker compound structures formed from said whiskers adapted to perform a predetermined function;
- a fourth structure adapted for separating at least a portion of said plurality of whisker compound structures from said substrate so as to prevent or minimize damage to said substrate; and
- a fifth structure adapted for collecting said separated portion of said whisker compound structures.

* * * * *